(12) United States Patent  (10) Patent No.: US 7,662,154 B2
Ribeiro  (45) Date of Patent: Feb. 16, 2010

(54) ANTERIOR CERVICAL PLATING SYSTEM

(75) Inventor: Helio Marcos Ribeiro, Newark, NJ (US)

(73) Assignee: Blackstone Medical, Inc., Springfield, MA (US)

( * ) Notice: Subject to any disclaimer, the term of this patent is extended or adjusted under 35 U.S.C. 154(b) by 403 days.

(21) Appl. No.: 11/228,117

(22) Filed: Sep. 16, 2005

(65) Prior Publication Data

US 2007/0083203 A1    Apr. 12, 2007

(51) Int. Cl.
    *A61B 17/80*    (2006.01)
(52) U.S. Cl. .................... 606/70; 606/289; 606/296
(58) Field of Classification Search ............ 606/60–61, 606/69–71, 295, 296, 280, 289, 291
    See application file for complete search history.

(56) References Cited

U.S. PATENT DOCUMENTS

| | | | |
|---|---|---|---|
| 6,152,927 A | 11/2000 | Farris et al. | |
| 6,193,721 B1 | 2/2001 | Michelson | |
| 6,224,602 B1 | 5/2001 | Hayes | |
| 6,383,186 B1 | 5/2002 | Michelson | |
| 6,398,783 B1 * | 6/2002 | Michelson | 606/70 |
| 6,428,542 B1 | 8/2002 | Michelson | |
| 6,503,250 B2 * | 1/2003 | Paul | 606/279 |
| 6,527,776 B1 | 3/2003 | Michelson | |
| 6,533,786 B1 | 3/2003 | Needham et al. | |
| 6,592,586 B1 | 7/2003 | Michelson | |
| 6,602,256 B1 | 8/2003 | Hayes | |
| 6,669,700 B1 | 12/2003 | Farris et al. | |
| 2001/0047172 A1 | 11/2001 | Foley et al. | |
| 2002/0120273 A1 | 8/2002 | Needham et al. | |
| 2004/0220566 A1 * | 11/2004 | Bray | 606/61 |
| 2004/0220571 A1 | 11/2004 | Assaker et al. | |
| 2005/0075633 A1 | 4/2005 | Ross | |
| 2008/0021470 A1 | 1/2008 | Ross | |

OTHER PUBLICATIONS

Search Report, European Application No. 06120789.0, dated Mar. 4, 2008, (5 pages).

* cited by examiner

*Primary Examiner*—Eduardo C Robert
*Assistant Examiner*—Elana B Fisher
(74) *Attorney, Agent, or Firm*—Kenyon & Kenyon LLP

(57) ABSTRACT

Disclosed are systems and methods for spinal fusion and particularly, anterior cervical plating systems with a toggle pivotally mounted to a bone plate with at least two degrees of freedom of movement. In a particular embodiment, each toggle plate is slidably attached and pivotally mounted to the bone plate by a locking screw having an axis such that in at least one slidable position each toggle plate can pivot relative to the axis of the locking screw in the bone plate.

32 Claims, 14 Drawing Sheets

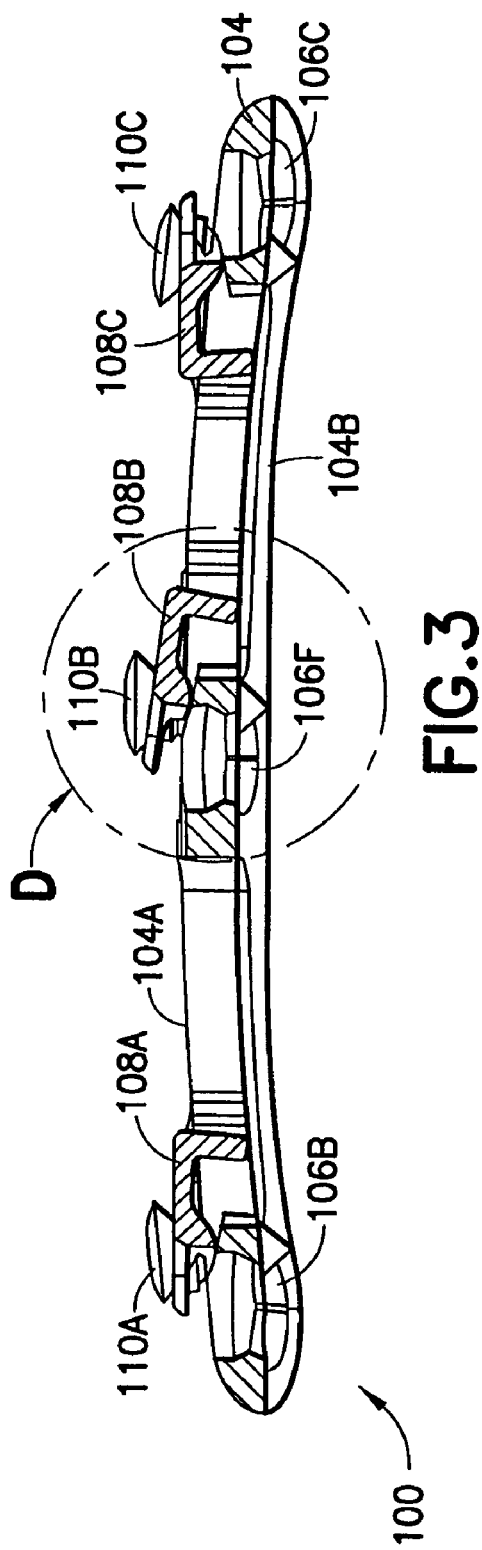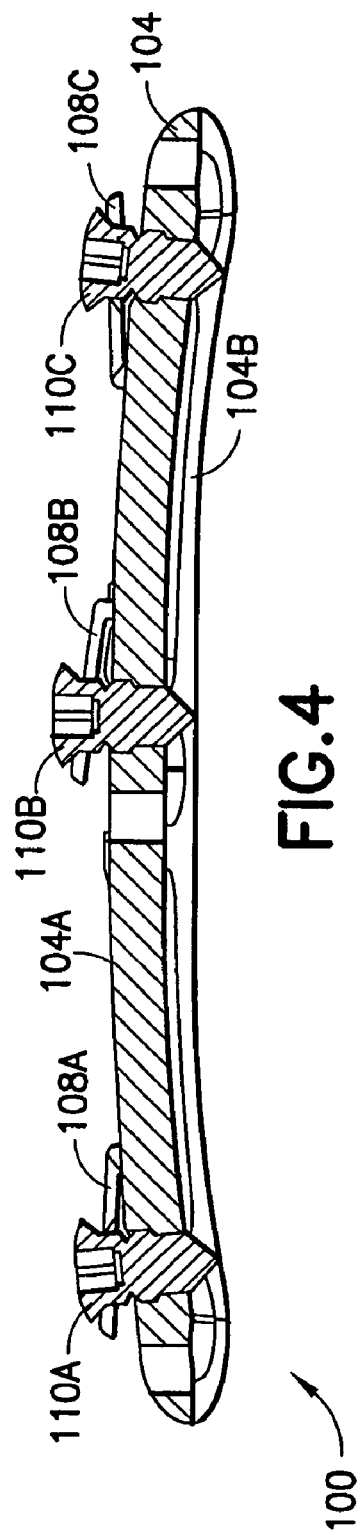

ANTERIOR CERVICAL PLATING SYSTEM

FIELD OF THE INVENTION

The present invention relates to systems and methods for spinal fusion.

More particularly, one embodiment of the present invention relates to an anterior cervical plating system.

For the purposes of describing and claiming the present invention, the term "plate" is intended to refer to any three-dimensional structure (i.e., not necessarily a flat structure). In this regard, such plate may be curved along one or more axis and may have one or more apertures or other features therein and/or thereon.

Further, for the purposes of describing and claiming the present invention, the term "aperture" is intended to refer to any hole or space (i.e., not necessarily round). In this regard, such an aperture may be round, oval, square, rectangular (or any other desired shape) and may be totally surrounded by material (e.g., a "hole" through an item) or may be partially surrounded by material (e.g., a "slot" or "indentation" at a perimeter of an item).

BACKGROUND OF THE INVENTION

Various systems directed to fusion of the spine have been proposed. Examples include the systems described in the following U.S. Patents issued to Gary Michelson: U.S. Pat. No. 6,527,776, entitled "Locking Element For Locking At Least Two Bone Screws To An Orthopedic Device"; U.S. Pat. No. 6,592,586, entitled "Single-Lock Anterior Cervical Plating System"; U.S. Pat. No. 6,428,542, entitled "Single-Lock Anterior Cervical Plate System"; U.S. Pat. No. 6,398,783, entitled "Multi-Lock Anterior Cervical Plate"; U.S. Pat. No. 6,383,186, entitled "Single-Lock Skeletal Plating System"; and U.S. Pat. No. 6,193,721, entitled "Multi-Lock Anterior Cervical Plating System".

Of note, each of the above patents appears to disclose a system in which one or more bone screws are held to the bone plate via a locking mechanism (such as a screw) which rotates relative to the bone plate.

Likewise, U.S. Pat. No. 6,152,927, entitled "Anterior Cervical Plating System" and U.S. Pat. No. 6,669,700, entitled "Anterior Cervical Plating System" appear to disclose a system in which one or more bone screws are held to the bone plate via a locking mechanism (such as a screw) which rotates relative to the bone plate.

Finally, each of U.S. Pat. No. 6,224,602, entitled "Bone Stabilization Plate With A Secured-Locking Mechanism For Cervical Fixation" and U.S. Pat. No. 6,533,786, entitled "Anterior Cervical Plating System" appears to disclose a system in which one or more bone screws are held to the bone plate via a locking mechanism which slides relative to the bone plate.

Of note, however, in these last two aforementioned systems it appears that each of the locking mechanisms is provided with only one degree of freedom, such that the locking mechanism may slide relative to the bone plate but may not be moved up or down relative to the bone plate (and relative to the bone screws within the bone plate). Thus, these last two aforementioned systems do not appear capable of providing pressure on bone screws which are disposed at varying depths relative to the bone plate.

BRIEF DESCRIPTION OF THE DRAWINGS

FIGS. 1-7 show various views of a fastener assembly according to an embodiment of the present invention (wherein the fastener assembly is shown without bone screws inserted therein and with the toggle plates in an open, or unlocked position). More particularly, FIG. 1 is a top view, FIG. 2 is a side view, FIG. 3 is a cross-sectional view taken along line B-B of FIG. 1, FIG. 4 is a cross-sectional view taken along line A-A of FIG. 1, FIG. 5 is a cross-sectional view taken along line C-C of FIG. 1, FIG. 6 shows detail portion D of FIG. 3, and FIG. 7 shows detail portion E of FIG. 5.

FIG. 8 is a top view, FIG. 9 is a side view, FIG. 10 is a cross-sectional view taken along line B-B of FIG. 8, FIG. 11 is a cross-sectional view taken along line E-E of FIG. 8, FIG. 12 is a cross-sectional view taken along line G-G of FIG. 8, FIG. 13 shows detail portion F of FIG. 11, and FIG. 14 shows detail portion H of FIG. 12.

Figure 1:
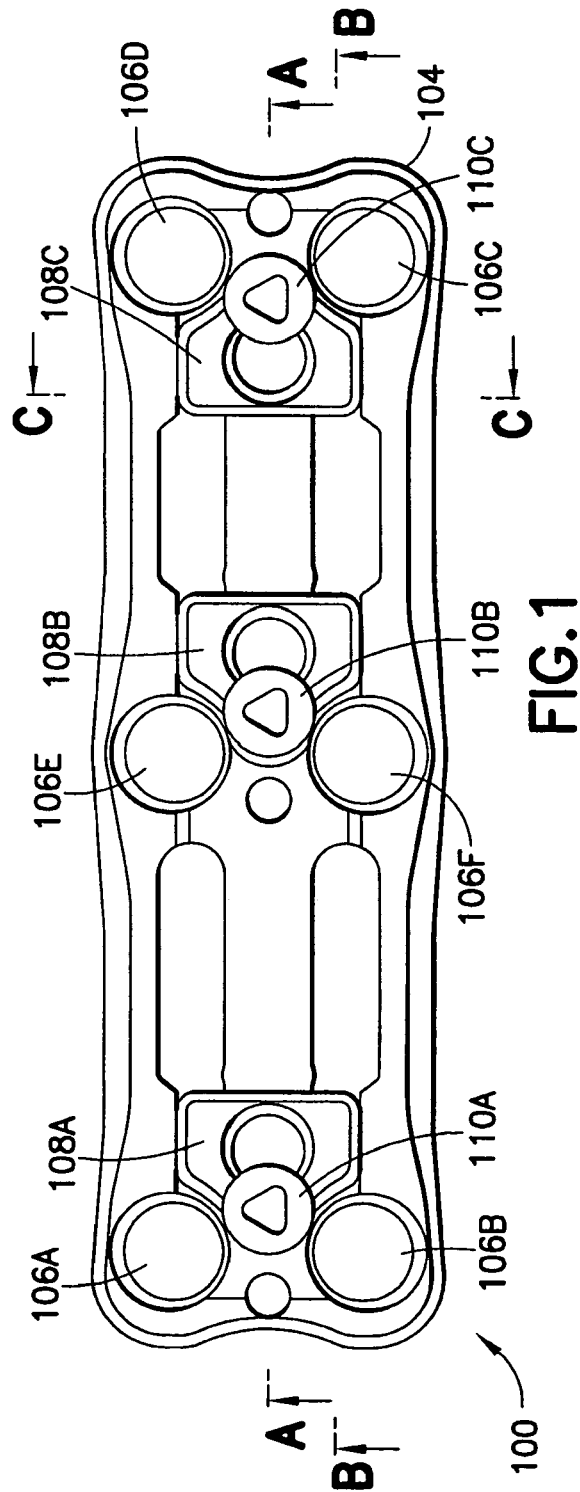
Figure 2:
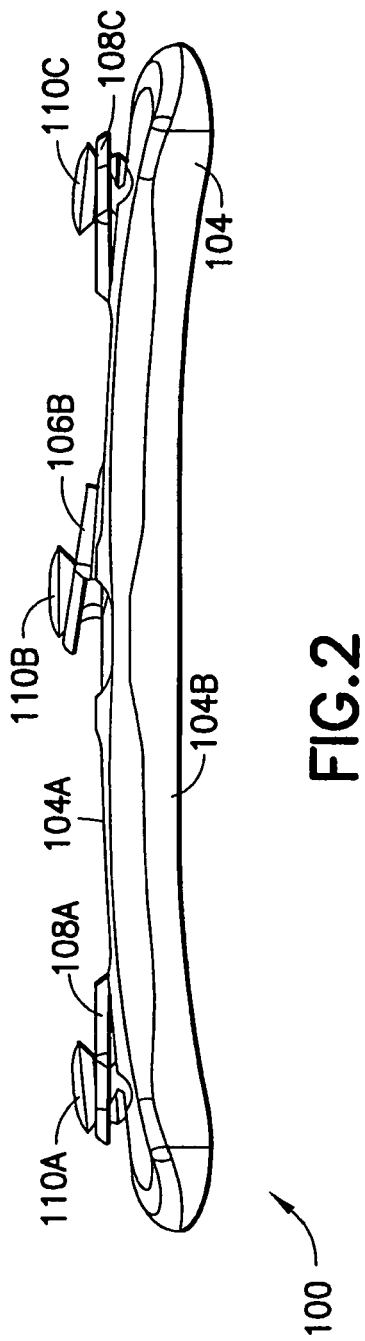
Figure 5:
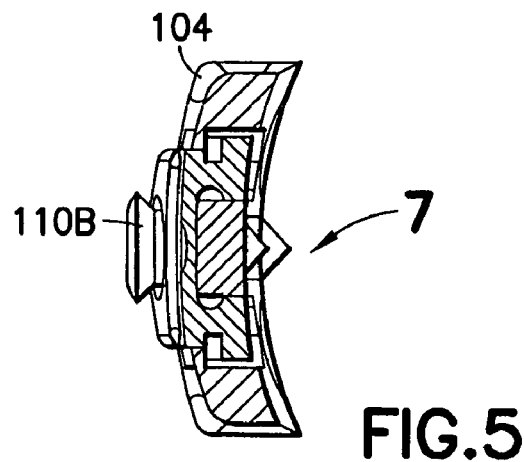
Figure 6:
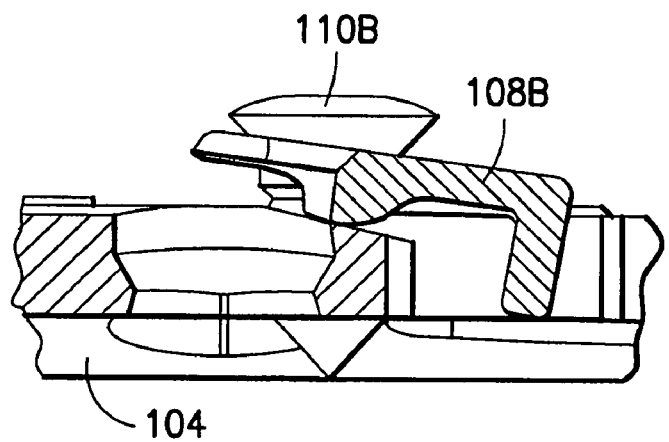
Figure 7:
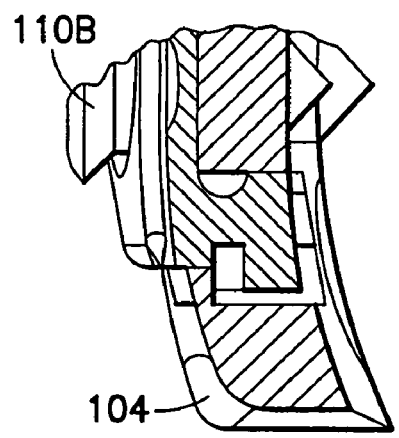
Figure 8:
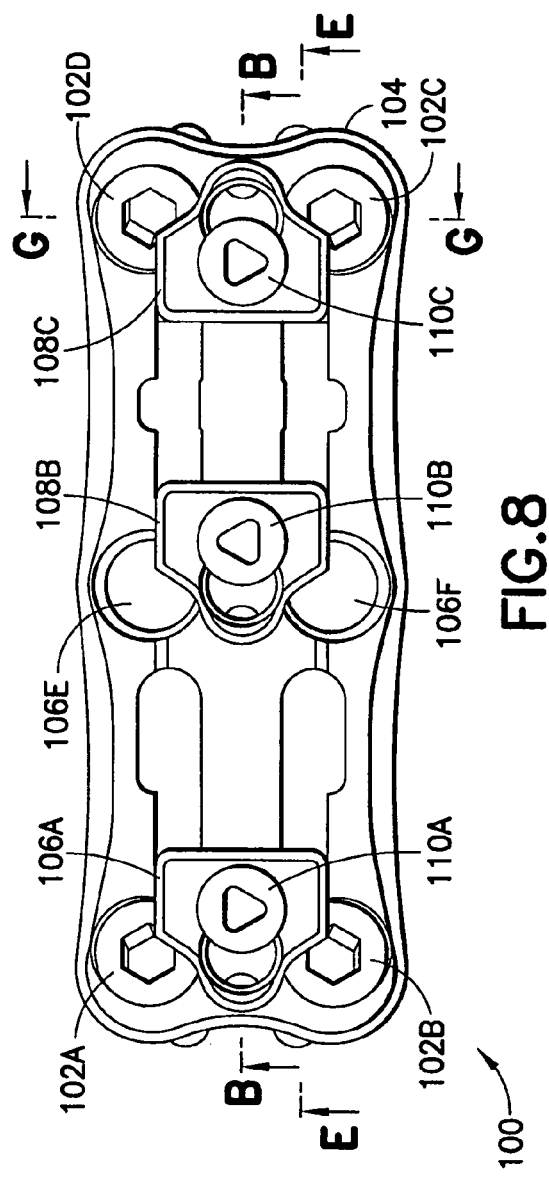
FIGS. 8-14 show various views of the fastener assembly of FIGS. 1-7 (wherein the fastener assembly is shown with bone screws inserted therein and with the toggle plates in a closed, or locked position). More particularly.
Figure 9:
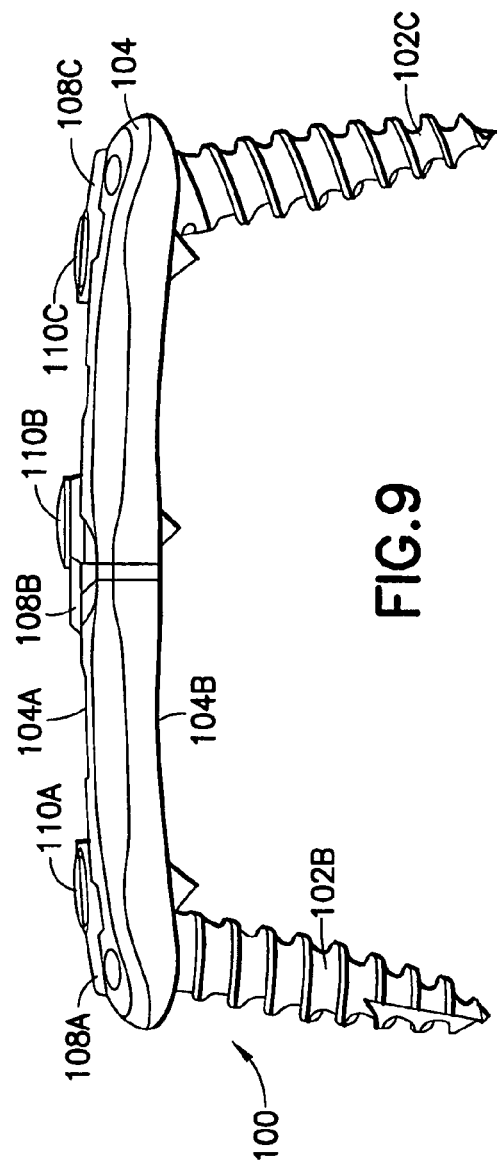
Figure 10:
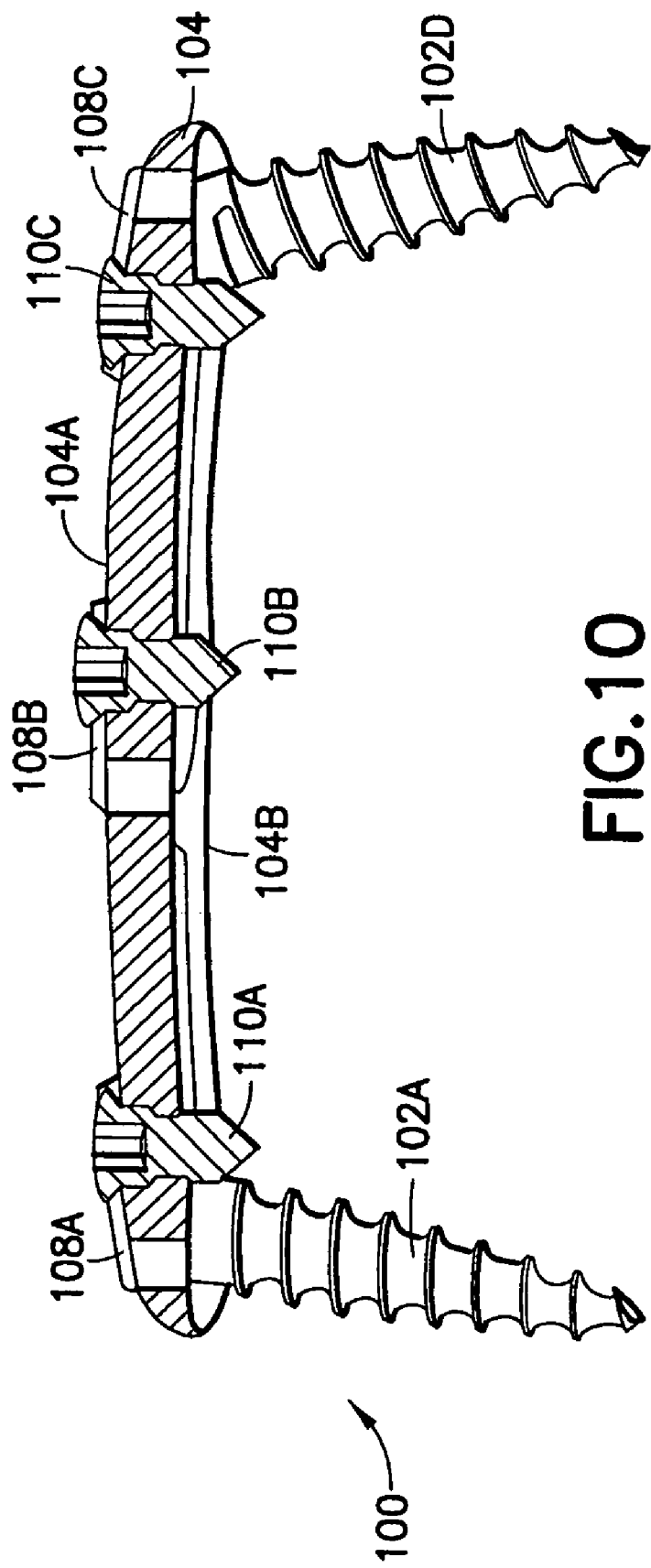
Figure 11:
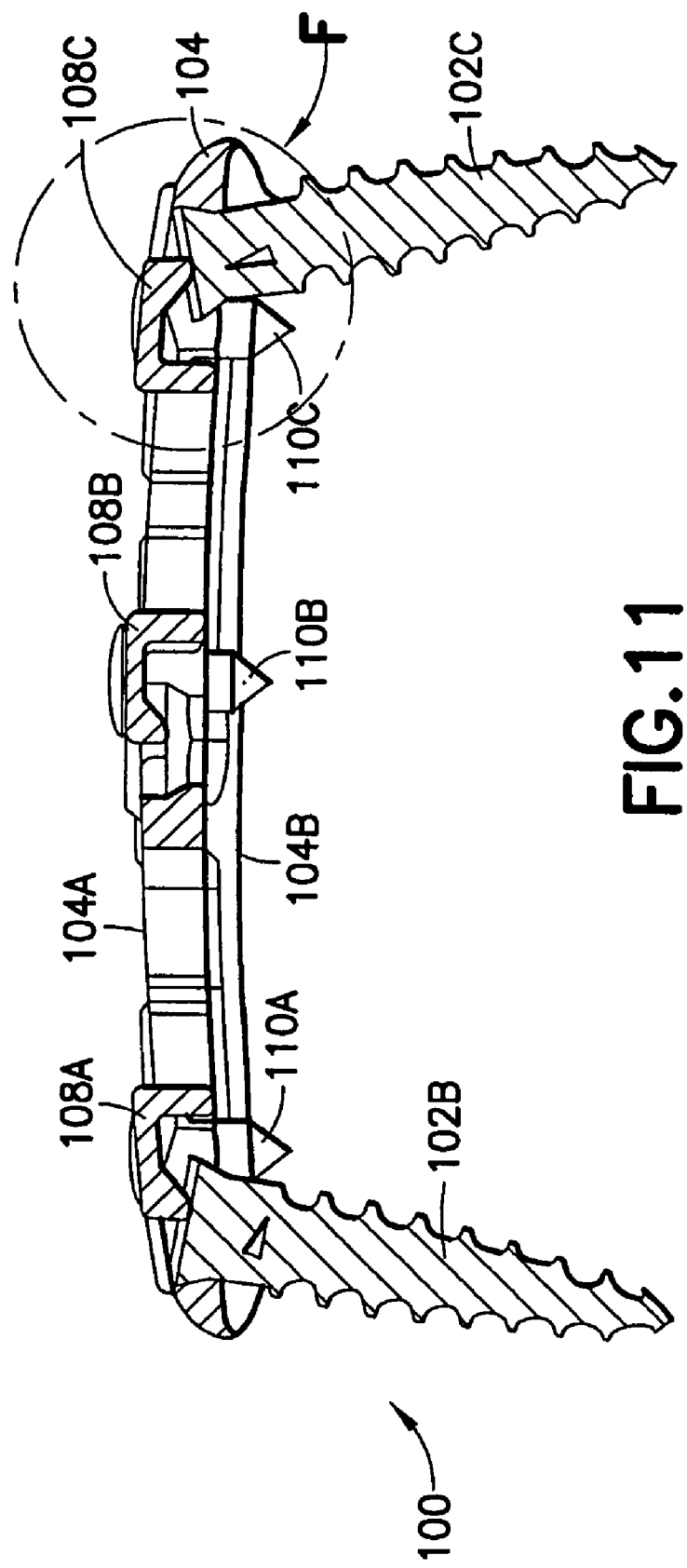
Figure 13:
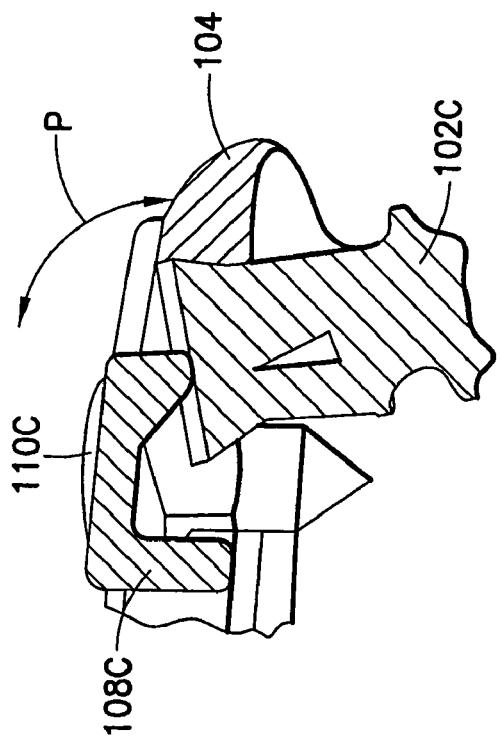
Figure 14:
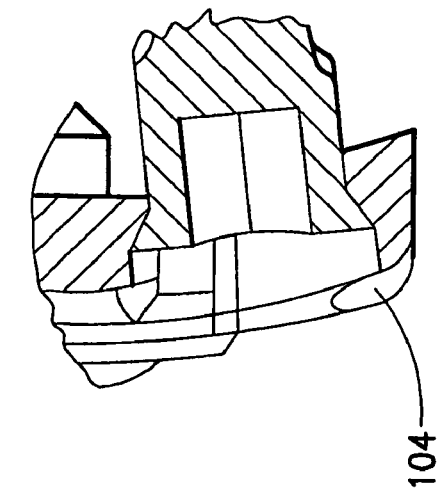
Figure 12:
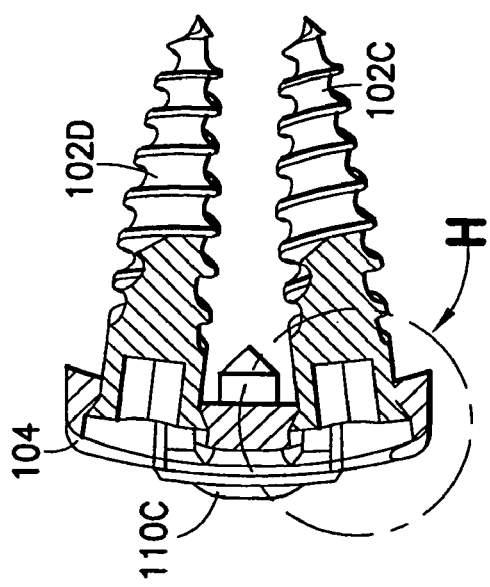

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, all of the measurements provided in the drawings are intended to be illustrative and not restrictive. Further still, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Referring now to FIGS. 1-14, a first embodiment of the present invention is shown. As seen in these FIGS., implant assembly 100 may be adapted to be fixed to a spine (not shown) using bone screws 102A-102D (see FIGS. 8-14). Of note, each bone screw may have a shank with a thread and a head with a feature for engagement with a driving mechanism, such as a screwdriver. Of further note, while 4 bone screws are shown here, any desired number may be used.

Further, plate member 104 may have apertures 106A-106F extending therethrough (wherein each aperture includes a first region sized to permit the shank of a respective bone screw but not the head of the respective bone screw to pass, and wherein each aperture includes a second region sized to permit both the shank of the respective bone screw and the head of the respective bone screw to pass).

Further still, implant assembly 100 may include toggle plates 108A-108C, wherein each toggle plate 108A-108C may be slidably attached to plate member 104 and wherein each toggle plate 108A-108C may be operatively associated with two of the bone screws (since only four bone screws are shown in this example, only toggle plates 108A and 108C are associated with bone screws in these drawings).

Of note, each toggle plate 108A-108C may be slideable to a first position (see FIGS. 1-7) in which each bone screw associated therewith may be inserted in a respective aperture such that the shank of each of the bone screws passes into the first region and the head of each of the bone screws remains in the second region.

Of further note, each toggle plate 108A-108C may be slideable to a second position (see FIGS. 8-14) in which the head of each bone screw associated therewith may be at least partially covered by the toggle plate.

Of note, the sliding of each toggle plate 108A-108C between the first position and the second position may, for example, be laterally along the length of plate member 104.

Finally, it is noted that each toggle plate 108A-108C may be pivotally mounted to plate member 104 (see pivot line "P" of FIG. 13) such that at least at the second slidable position each toggle plate 108A-108C can pivot relative to the plate member 104 (i.e., each toggle plate 108A-108C is thus provided with at least two degrees of freedom of movement relative to plate member 104). It is in this last regard, in particular, that this embodiment of the present invention provides a mechanism via which pressure may be applied to bone screws which are disposed at varying depths relative to the plate member.

Of course, by operating as described above, it can be seen that each bone screw 102A-102D may be blocked from backing-out of the plate member 104 (and the underlying bone) while one of the toggle plates associated therewith (i.e., associated with a given bone screw) is in the second slidable position. Conversely, each bone screw 102A-102D may be removed from the plate member 104 (and the underlying bone) while one of the toggle plates associated therewith (i.e., associated with a given bone screw) is in the first slidable position. In this regard, visualization of lock position is provided Again referring to FIGS. 1-14, it is seen that this embodiment may comprise toggle plate locking screws 110A-110C (wherein each toggle plate locking screw 110A-110C may be adapted to pass through each toggle plate 108A-108C) into a respective threaded hole in plate member 104. In this regard, each toggle plate locking screw 110A-110C may be adapted to press down on a respective one of the toggle plates 108A-108C to pivot the toggle plate downward (and onto a respective bone screw) when the toggle plate is in the second slidable position and the associated toggle plate locking screw is rotated in a first direction. Of course, unlocking (e.g., for bone screw removal) is accomplished by loosening a toggle plate locking screw 110A-110C and pivoting/sliding the toggle plate back.

Again referring to FIGS. 1-14, it is seen that in this embodiment plate member 104 may have a top surface 104A and a bottom surface 104B, wherein the first region of the aperture is adjacent bottom surface 104B of plate member 104, and wherein the second region of the aperture is adjacent top surface 104A of the plate member 104. In this regard, each bone screw 102A-102D may be inserted from top surface 104A of plate member 104 towards bottom surface 104B of plate member 104. In one example (which example is intended to be illustrative and not restrictive), bottom surface 104B of plate member 104 may be contoured to substantially match a contour of the bone to which the implant assembly 100 is affixed. In another example (which example is intended to be illustrative and not restrictive), bottom surface 104B of plate member 104 may be curved along at least one axis. In another example (which example is intended to be illustrative and not restrictive), bottom surface 104B of plate member 104 may be curved along a first axis and a second axis. In another example (which example is intended to be illustrative and not restrictive), the first axis and the second axis may be substantially orthogonal to one another. In another example (which example is intended to be illustrative and not restrictive), the implant assembly may be used for fusing at least two vertebral bodies.

In another example (which example is intended to be illustrative and not restrictive), the implant assembly may be used in an anterior cervical plating procedure.

In another example (which example is intended to be illustrative and not restrictive), the implant assembly may include between four and ten apertures for receiving therein between four and ten bone screws.

In another example (which example is intended to be illustrative and not restrictive), two of the bone screws may be screwed into each of the vertebral bodies through two of the apertures.

In another example (which example is intended to be illustrative and not restrictive), the thinner region of each bone screw may include a threaded shank and the thicker region of each bone screw may include a head.

In another example (which example is intended to be illustrative and not restrictive), the present invention may be constructed to be anatomically friendly and to have any desired minimum and maximum dimensions (e.g., made very narrow to safely accommodate narrow vertebral bodies).

In another example (which example is intended to be illustrative and not restrictive), the present invention may provide ease of use due to one or more of the following features: (a) integral toggle plate mechanism; (b) one step locking and unlocking; (c) self-drilling bone crews (e.g., allow a surgeon to punch or drill and place bone screws); (d) streamlined instrument tray.

In another example (which example is intended to be illustrative and not restrictive), the present invention may provide ease of use by utilizing constrained bone screws and/or unconstrained bone screws (which allow variable angle screw placement).

In another example (which example is intended to be illustrative and not restrictive), the profile and screw placement associated with the plate member may be as follows:

Profile
  Thickness: 2.5 mm
  Width: 15.0 mm
  Lordosed: Yes
Variable Angle Screw Placement
  −5 degree to +12 degree caudal/cephalad variability for superior/inferior bone screws
  +/−5 degree caudal/cephalad variability for intermediate bone screws
  6 degrees convergent (lateral to medial)

Figure 15:
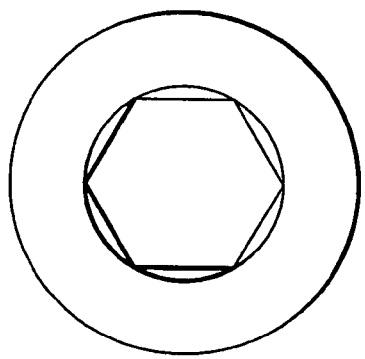
FIGS. 15-18 show details of two different types of bone screws which may be utilized with the present invention.
Figure 16:
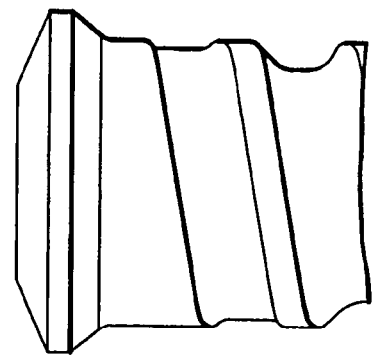
Figure 17:
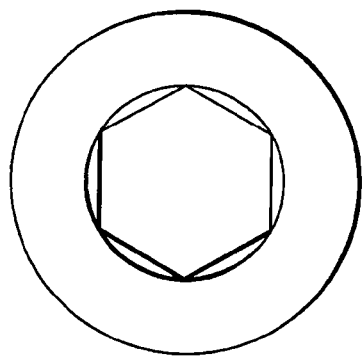
Figure 18:
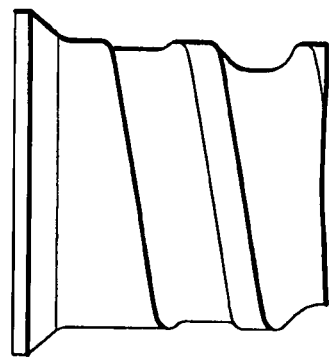

In another example (which example is intended to be illustrative and not restrictive), the plate member may have a length selected from the following configurations:

Lengths—1 to 4 level plates (measured from the caudad and cephalad edges of the plate)
  1 level: 18 mm-36 mm in 2 mm increments
  2 level: 34 mm-54 mm in 2 mm increments
  3 level: 46 mm-70 mm in 2 mm increments and 74 mm-90 mm in 4 mm increments
  4 level: 94 mm-122 mm in 4 mm increments In another example (which example is intended to be illustrative and not restrictive), the bone screw characteristics may be selected from the following configurations:

Primary Bone Screws—fixed and variable angle (screw length measured from the tip of the screw to the underside of the plate when installed)
  Lengths(mm)and colors: 10-teal; 12-magenta; 14-gold; 16-blue; 18-seafoam
  Major Diameter (mm): 4.1 (tapered transitioning to a constant diameter)
  Minor Diameter: tapered
  Self-drilling and self-tapping
Rescue Bone Screws—fixed and variable angle (screw length measured from the tip of the screw to the underside of the plate when installed)
  Lengths (mm) and colors: 10-teal; 12-magenta; 14-gold; 16-blue; 18-seafoam
  Screw Heads are silver, shafts are colored according to length
  Major Diameter (mm): 4.5 (tapered transitioning to a constant diameter)
  Minor Diameter: tapered
  Self-drilling and self-tapping Referring now to FIGS. 15-18, details of two different types of bone screws which may be utilized with the present invention are shown. More particularly, FIG. 15 shows a top view of the head of a fixed or constrained bone screw (that is, a bone screw whose angular position can not be changed while locked within the locking plate); FIG. 16 shows a side view of the head and part of the shank of the fixed bone screw of FIG. 15; FIG. 17 shows a top view of the head of a variable or unconstrained bone screw (that is, a bone screw whose angular position can be changed while locked within the locking plate); and FIG. 18 shows a side view of the head and part of the shank of the variable bone screw of FIG. 17.

Referring now to FIGS. 19-30 a number of instruments which may be utilized in connection with the present invention are shown.

Figure 19:
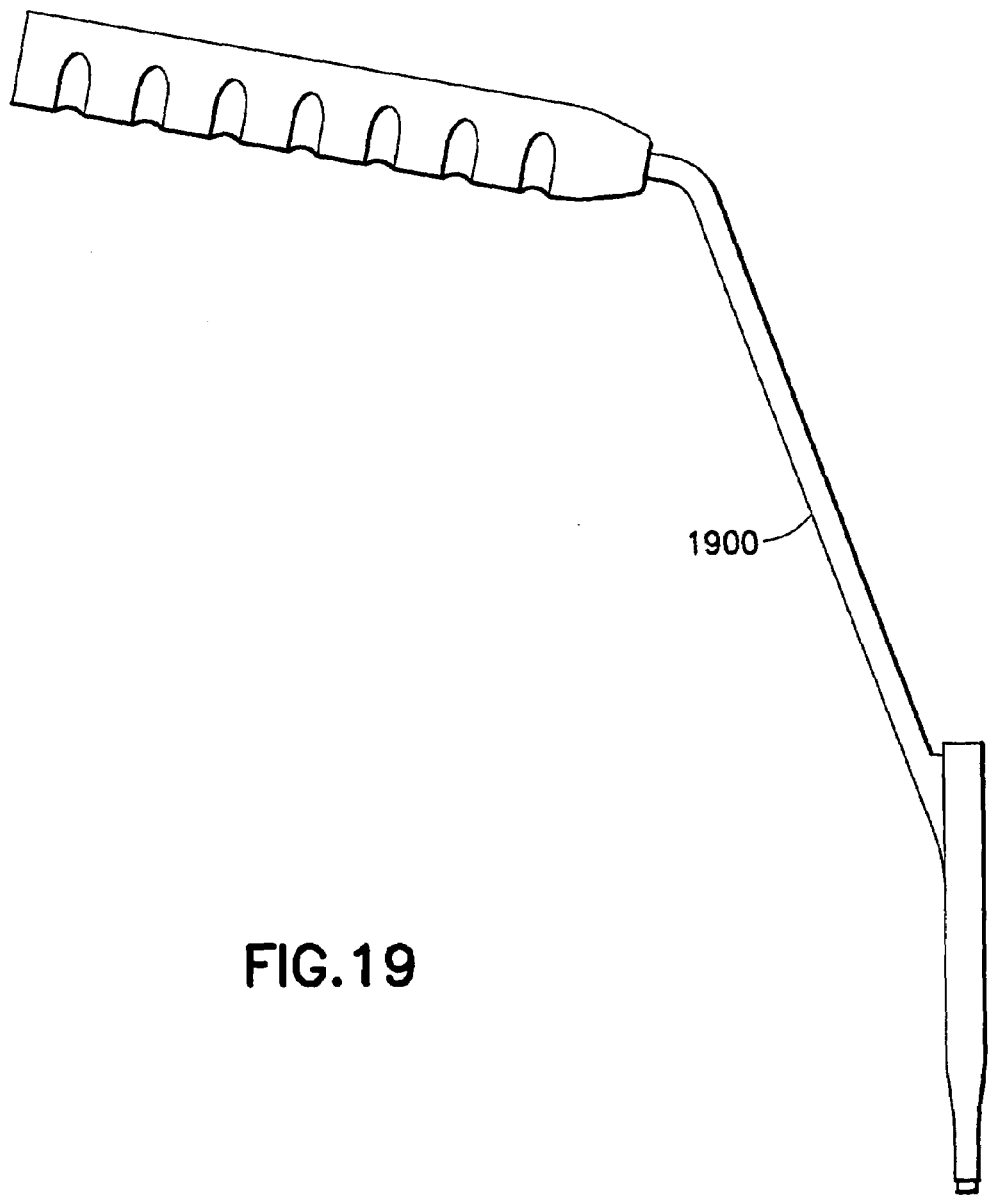
FIGS. 19-30 show a number of instruments which may be utilized in connection with the present invention.

More particularly, FIG. 19 depicts freehand drill guide 1900 (which may limit drilling depth and restrict angulation when preparing bone to receive a bone screw).

Figure 20:
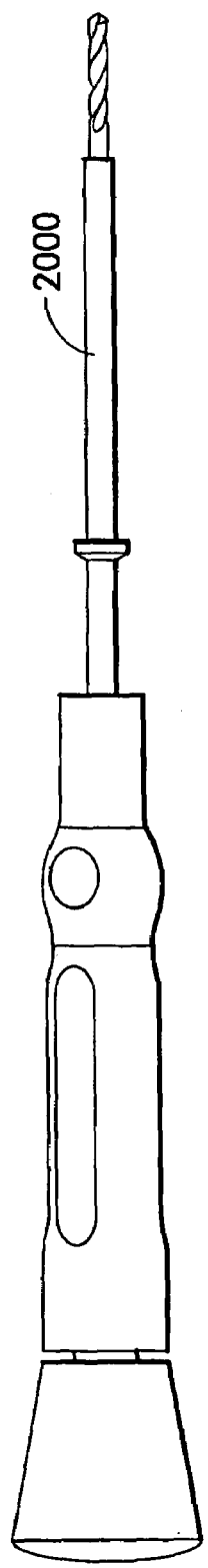

Further, FIG. 20 depicts drill 2000 (which may utilize a modular handle or power) and which may be provided, for example, in 10 mm to 18 mm sizes (fixed depth with positive stop).

Figure 21:
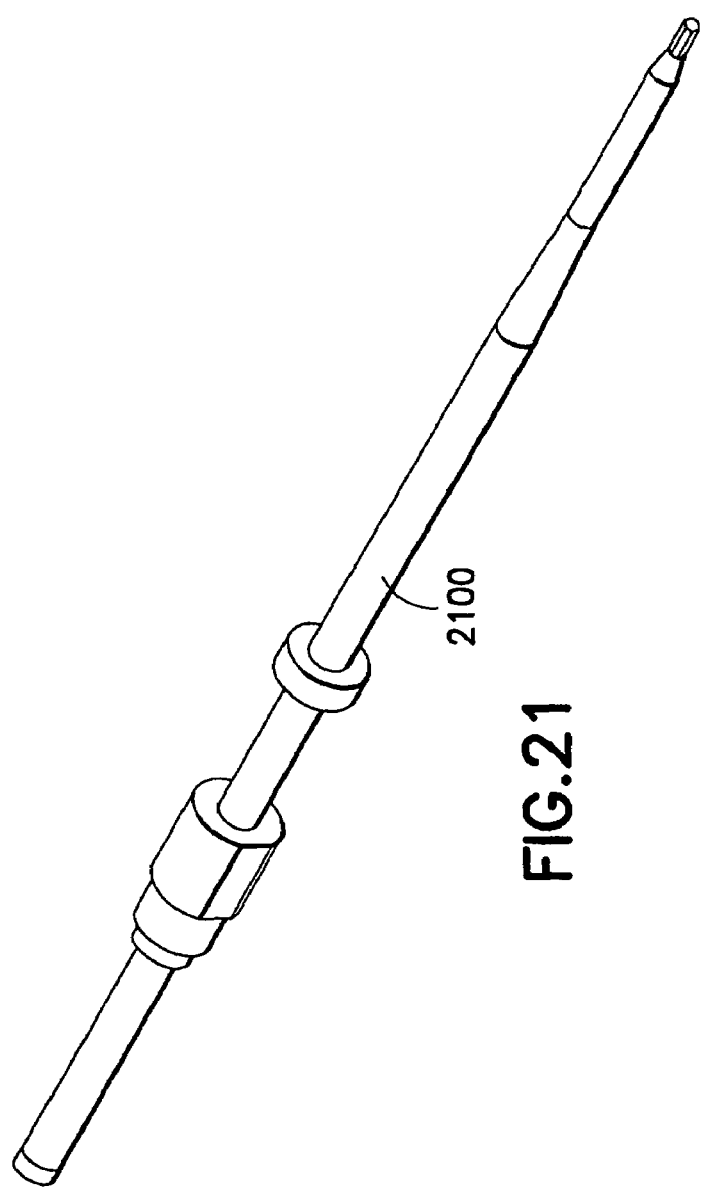
Figure 22:
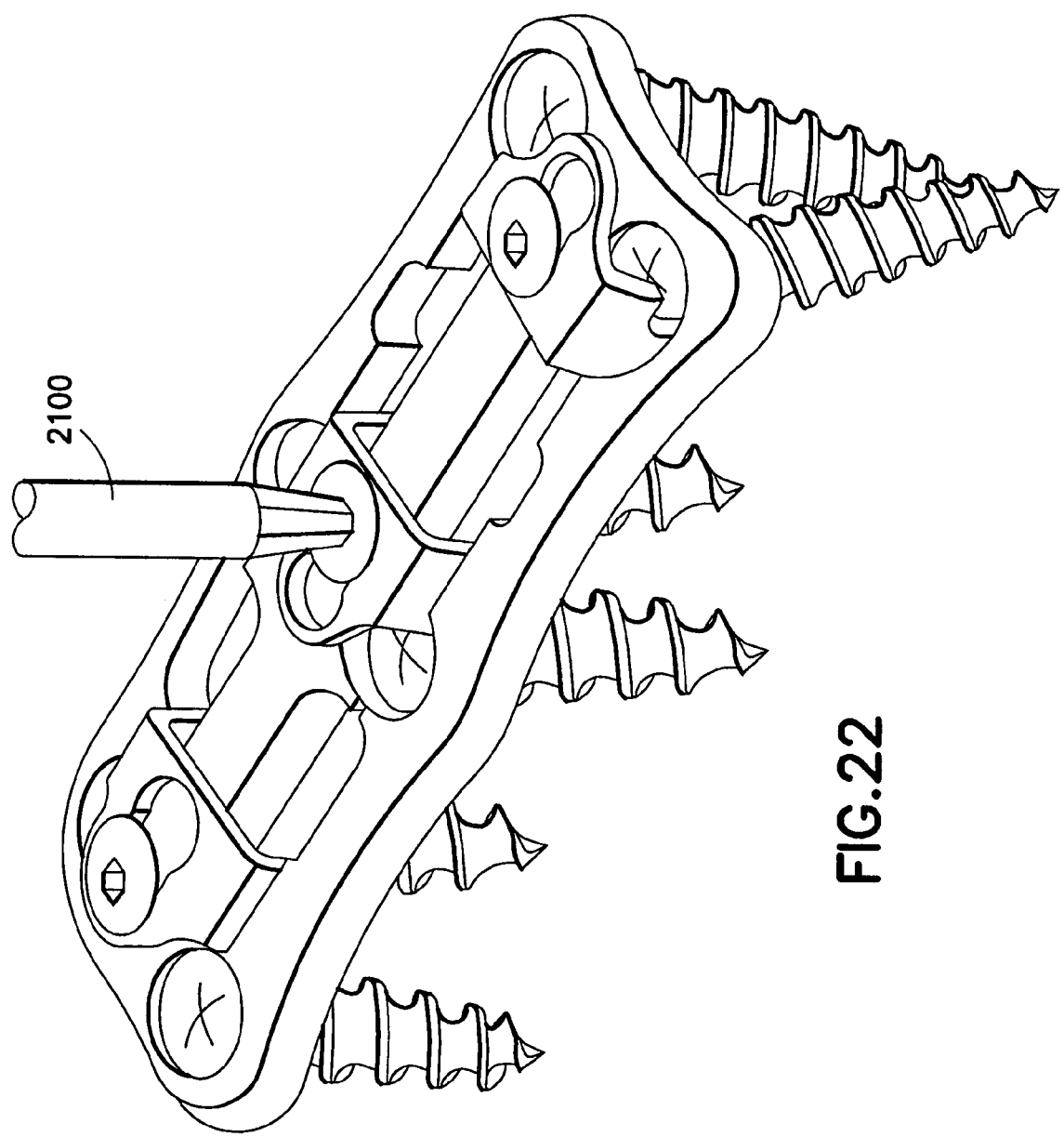

Further still, FIG. 21 depicts tri-lobe screw driver 2100, which may be used to tighten and loosen the toggle plate locking screws (see detail of FIG. 22) and which may utilize a torque handle for limiting torque.

Figure 23:
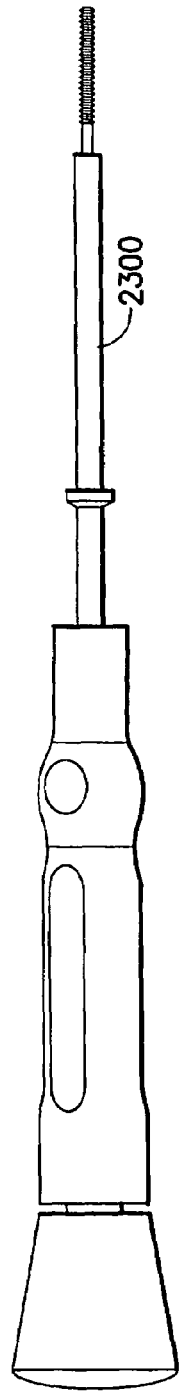

Further still, FIG. 23 depicts tap 2300, which may be, for example, 10 mm length with positive stop, which may be single use, and which may be used with a modular handle.

Figure 24:
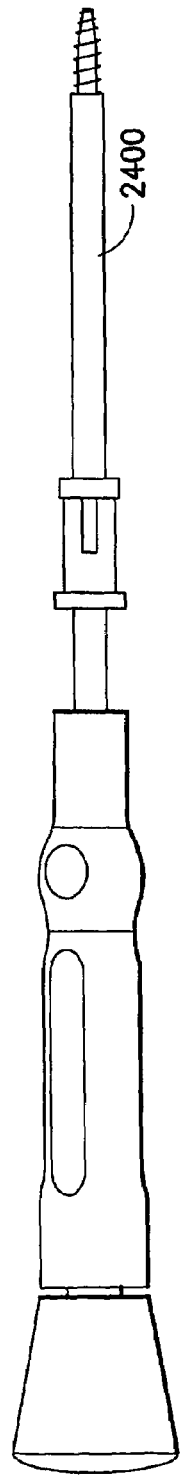

Further still, FIG. 24 depicts screw driver 2400, which may be, for example, of one length (with a stop to indicate screw depth), which may have a spring-loaded tip for screw security, and which may be used with a modular handle.

Figure 25:
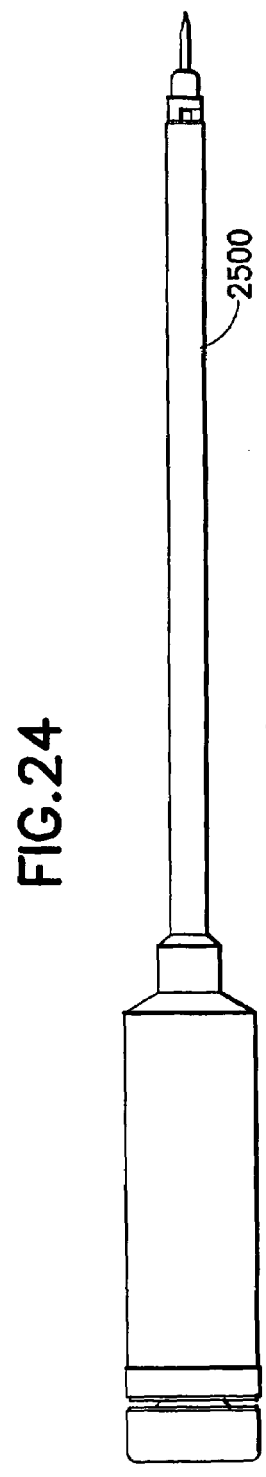
Figure 26:
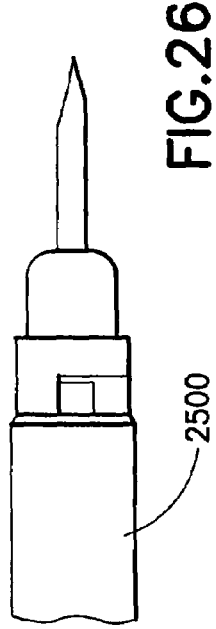

Further still, FIG. 25 depicts tack holder 2500, which may allow easy insertion and removal of temporary tacks (see detail of FIG. 26) and which may permit rotation of a beveled knob on the instrument handle to secure or release the tack therefrom.

Figure 27:
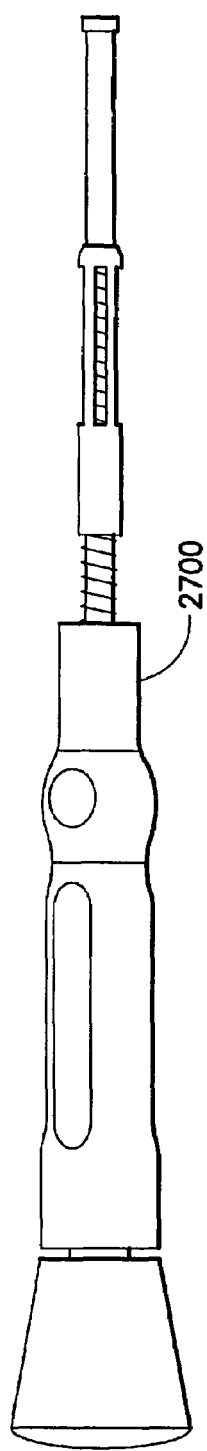
Figure 28:
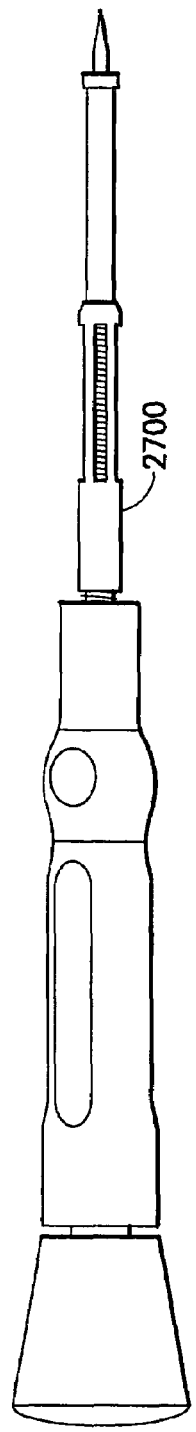

Further still, FIG. 27 depicts a first bone awl 2700, which may provide, for example, 11 mm penetration, which may have a spring retracted sleeve (see sleeve in retracted position in FIG. 28), and which may be used with a modular handle.

Figure 29:
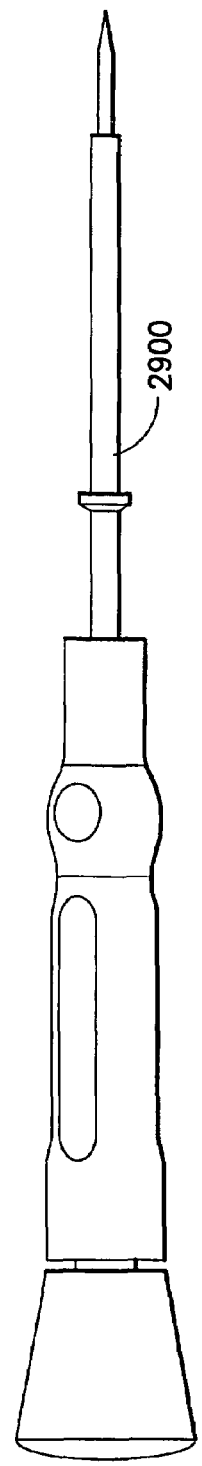

Further still, FIG. 29 depicts a second bone awl 2900, which may provide, for example, 5 mm penetration with drill guide (tip length: 5 mm) and which may be used with a drill guide and a modular handle.

Figure 30:
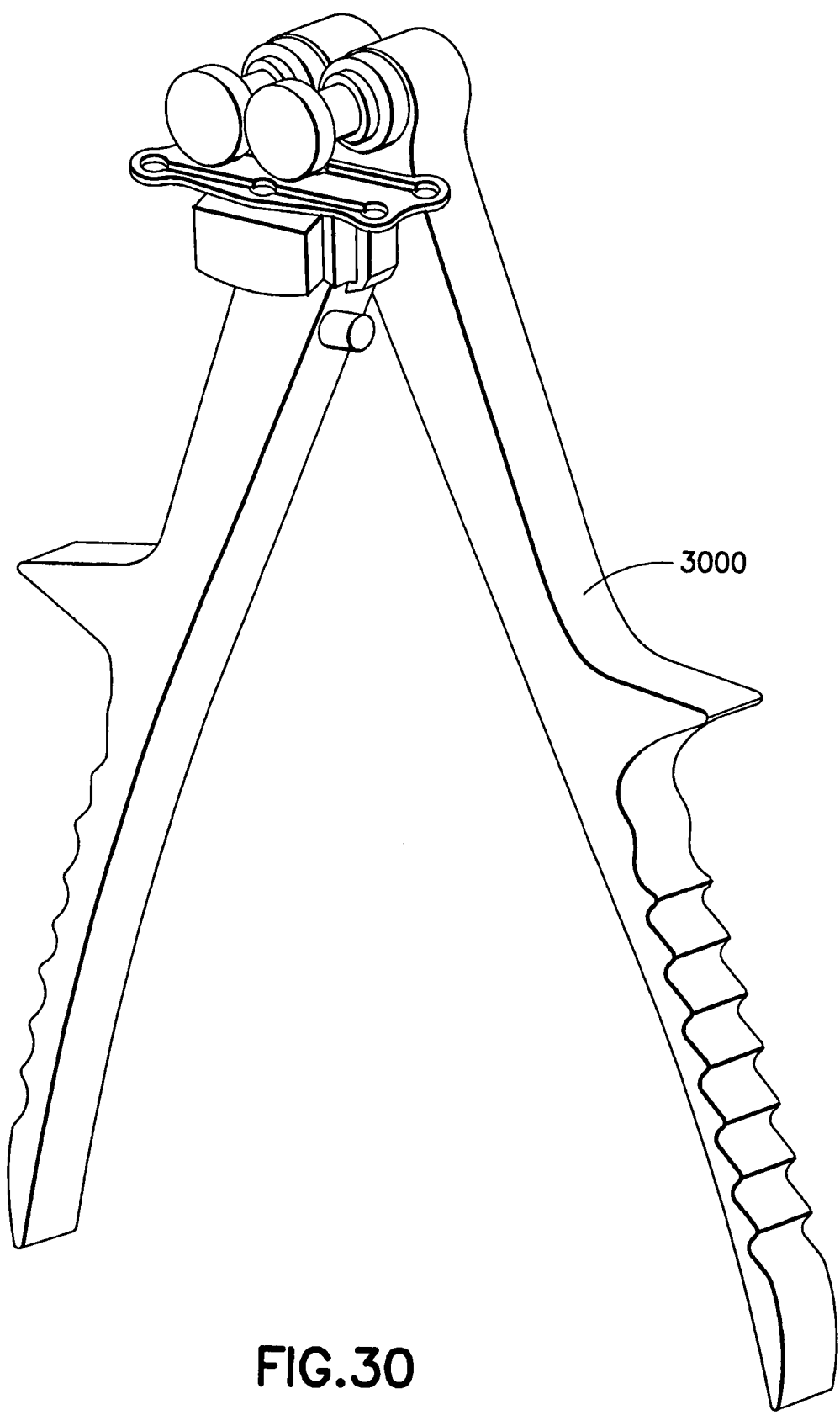

Further still, FIG. 30 depicts plate bender 3000, which may be used to contour the plate member.

While a number of embodiments of the present invention have been described, it is understood that these embodiments are illustrative only, and not restrictive, and that many modifications may become apparent to those of ordinary skill in the art. For example, any desired number of bone screws may be used to fix the device to any desired number of vertebral bodies (and the present invention may be placed at any desired level(s) of the spine). Further, the present invention may be used in conjunction with a spinal rod implantation. Further still, any element described herein may be provided in any desired size (e.g., any element described herein may be provided in any desired custom size or any element described herein may be provided in any desired size selected from a "family" of sizes, such as small, medium, large). Further still, one or more of the components of the implant assembly may be made from any of the following materials: (a) any biocompatible material (which biocompatible material may be treated to permit bone ingrowth or prohibit bone ingrowth—depending upon the desire of the surgeon); (b) a plastic; (c) a fiber; (d) a polymer; (e) a metal (a pure metal such as titanium and/or an alloy such as Ti—Al—Nb, Ti-6Al-4V, stainless steel); (f) any combination thereof. Further still, the toggle plates may be slid between positions by pushing, such as with a finger, or by application of a tool or other device. Further still, any steps described herein may be carried out in any desired order (and any desired steps may be added and/or eliminated).

What is claimed is:

1. An implant assembly adapted to be fixed to a spine using at least four bone screws, each bone screw having a shank and a head, wherein the implant assembly comprises: a plate member, wherein the plate member has at least four apertures extending therethrough, wherein each aperture includes a first region sized to permit the shank of a respective bone screw but not the head of the respective bone screw to pass, and wherein each aperture includes a second region sized to permit both the shank of the respective bone screw and the head of the respective bone screw to pass; and at least two toggle plates, wherein each toggle plate is slidably attached and pivotally mounted to the plate member by a locking screw having an axis and wherein each toggle plate is operatively associated with two of the bone screws; wherein each toggle plate is slideable to a first position in which each bone screw associated therewith may be inserted in the aperture such that the shank of the bone screw passes into the first region and the head of the bone screw remains in the second region; wherein each toggle plate is slideable to a second position in which the head of each bone screw associated therewith is at least partially covered by the toggle plate; wherein each toggle plate is pivotally mounted to the plate member such that at least at the second slidable position each toggle plate can pivot relative to the axis of the locking screw in the plate member; and wherein the locking screw causes pivotal movement upon tightening.

2. The implant assembly of claim 1, wherein the plate member has a top surface and a bottom surface, wherein the first region of the aperture is adjacent the bottom surface of the plate member, and wherein the second region of the aperture is adjacent the top surface of the plate member.

3. The implant assembly of claim 2, wherein each bone screw is inserted from the top surface of the plate member towards the bottom surface of the plate member.

4. The implant assembly of claim 3, wherein the bottom surface of the plate member is contoured to substantially match a contour of the bone to which the plate member is affixed.

5. The implant assembly of claim 4, wherein the bottom surface of the plate member is curved along at least one axis.

6. The implant assembly of claim 5, wherein the bottom surface of the plate member is curved along a first axis and a second axis.

7. The implant assembly of claim 6, wherein the first axis and the second axis are substantially orthogonal to one another.

8. The implant assembly of claim 1, wherein the implant assembly is used for fusing at least two vertebral bodies.

9. The implant assembly of claim 8, wherein the implant assembly is used in an anterior cervical plating procedure.

10. The implant assembly of claim 8, wherein the implant assembly includes between four and ten apertures for receiving therein between four and ten respective bone screws.

11. The implant assembly of claim 8, wherein two of the bone screws are screwed into each of the vertebral bodies through two of the apertures.

12. The implant assembly of claim 1, wherein the shank of each bone screw is threaded.

13. An implant assembly adapted to be fixed to a spine using at least four bone screws, each bone screw having a shank and a head, wherein the implant assembly comprises: a plate member, wherein the plate member has at least four apertures extending therethrough, wherein each aperture includes a first region sized to permit the shank of a respective bone screw but not the head of the respective bone screw to pass, and wherein each aperture includes a second region sized to permit both the shank of the respective bone screw and the head of the respective bone screw to pass; and at least two toggle plates; wherein each toggle plate is slidably attached and pivotally mounted to the plate member by a locking screw having an axis such that each toggle plate is operatively associated with two of the bone screws; wherein each toggle plate has at least two degrees of freedom of movement relative to the plate member; wherein the first degree of freedom of movement for each toggle plate is sliding movement between a first position in which each bone screw associated with the toggle plate may be inserted in the aperture such that the shank of each of the bone screws passes into the first region and the head of each of the bone screws remains in the second region and a second position in which the head of each bone screw associated with the toggle plate is at least partially covered by the toggle plate; wherein the second degree of freedom of movement for each toggle plate is pivoting movement relative to the axis of the locking screw in the plate member at least when the toggle plate is in the section position; and wherein the locking screw causes the pivoting movement upon tightening.

14. The implant assembly of claim 13, wherein the plate member has a top surface and a bottom surface, wherein the first region of the aperture is adjacent the bottom surface of the plate member, and wherein the second region of the aperture is adjacent the top surface of the plate member.

15. The implant assembly of claim 14, wherein each bone screw is inserted from the top surface of the plate member towards the bottom surface of the plate member.

16. The implant assembly of claim 15, wherein the bottom surface of the plate member is contoured to substantially match a contour of the bone to which the plate member is affixed.

17. The implant assembly of claim 16, wherein the bottom surface of the plate member is curved along at least one axis.

18. The implant assembly of claim 17, wherein the bottom surface of the plate member is curved along a first axis and a second axis.

19. The implant assembly of claim 18, wherein the first axis and the second axis are substantially orthogonal to one another.

20. The implant assembly of claim 13, wherein the implant assembly is used for fusing at least two vertebral bodies.

21. The implant assembly of claim 20, wherein the implant assembly is used in an anterior cervical plating procedure.

22. The implant assembly of claim 20, wherein the implant assembly includes between four and ten apertures for receiving therein between four and ten respective bone screws.

23. The implant assembly of claim 20, wherein two of the bone screws are screwed into each of the vertebral bodies through two of the apertures.

24. The implant assembly of claim 13, wherein the shank of each bone screw is threaded.

25. An implant assembly adapted to be fixed to a spine using at least one bone screw having a shank and a head, wherein the implant assembly comprises: a plate member, wherein the plate member has at least one aperture, wherein the aperture includes a first region sized to permit the shank of the bone screw but not the head of the bone screw to pass, and wherein the aperture includes a second region sized to permit both the shank of the bone screw and the head of the bone screw to pass; and at least one toggle plate; wherein the toggle plate is slidably attached and pivotally mounted to the plate member by a locking screw having an axis such that the toggle plate is operatively associated with the bone screw; wherein the toggle plate has at least two degrees of freedom of movement relative to the plate member; wherein the first degree of freedom of movement for the toggle plate is sliding movement between a first position in which the bone screw may be inserted in the aperture such that the shank of the bone screw passes into the first region and the head of the bone screw remains in the second region and a second position in which the head of the bone screw is at least partially covered by the toggle plate; wherein the second degree of freedom of movement for the toggle plate is pivoting movement relative to the axis of the locking screw in the plate member at least when the toggle plate is in the second position; and wherein the locking screw causes the pivoting movement upon tightening.

26. The implant assembly of claim 25, wherein the plate member has a top surface and a bottom surface, wherein the first region of the aperture is adjacent the bottom surface of the plate member, and wherein the second region of the aperture is adjacent the top surface of the plate member.

27. The implant assembly of claim 26, wherein the bone screw is inserted from the top surface of the plate member towards the bottom surface of the plate member.

28. The implant assembly of claim 27, wherein the bottom surface of the plate member is contoured to substantially match a contour of the bone to which the plate member is affixed.

29. The implant assembly of claim 28, wherein the bottom surface of the plate member is curved along at least one axis.

30. The implant assembly of claim 29, wherein the bottom surface of the plate member is curved along a first axis and a second axis.

31. The implant assembly of claim 30, wherein the first axis and the second axis are substantially orthogonal to one another.

32. The implant assembly of claim 25, wherein the implant assembly is used for fusing at least two vertebral bodies.

* * * * *

UNITED STATES PATENT AND TRADEMARK OFFICE
CERTIFICATE OF CORRECTION

PATENT NO.        : 7,662,154 B2
APPLICATION NO. : 11/228117
DATED             : February 16, 2010
INVENTOR(S)       : Helio Marcos Ribeiro It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 811 days.

Signed and Sealed this

Thirtieth Day of November, 2010

David J. Kappos
*Director of the United States Patent and Trademark Office*